(12) United States Patent
Smith

(10) Patent No.: US 8,954,284 B1
(45) Date of Patent: Feb. 10, 2015

(54) PRELIOPHIC MOLECULAR USING ELECTRIC FIELDS AND GRADIENTS FOR MANIPULATING MOLECULES

(76) Inventor: Roulette W. Smith, Santa Barbara, CA (US)

( * ) Notice: Subject to any disclaimer, the term of this patent is extended or adjusted under 35 U.S.C. 154(b) by 530 days.

(21) Appl. No.: 12/925,728

(22) Filed: Oct. 27, 2010

Related U.S. Application Data

(62) Division of application No. 10/879,627, filed on Jun. 29, 2004, now Pat. No. 7,826,974.

(51) Int. Cl.
*G01N 33/50* (2006.01)
*G01N 33/00* (2006.01)

(52) U.S. Cl.
USPC ............................................. 702/19; 702/22

(58) Field of Classification Search
CPC ............................ G06F 19/12; G01N 30/0005
See application file for complete search history.

*Primary Examiner* — Eric S Dejong
(74) *Attorney, Agent, or Firm* — Richard Esty Peterson

(57) ABSTRACT

Methods of inducing movement and interaction of molecules in an electric field of an electrophoretic device that is configured to cause molecules to move on a convergent path to mimic a living cell. The electrophoretic device is constructed to support an isoelectric focusing medium, such as a gel on a gel plate with spaced charged poles having different configurations to induce non-parallel migration, and in particular to induce convergent migration wherein spacially separated groups of like-kind molecules are driven on pathways to proximity with other group or groups of like-kind molecules. In this manner researchers may devise experiments with multiple substances to track pathways of interaction during osmotic diffusion and polar directed migration through the medium that simulates pathways in a biological cell. The experiment with select substances may be conducted with controlled variations in medium, potential and temperature.

16 Claims, 5 Drawing Sheets

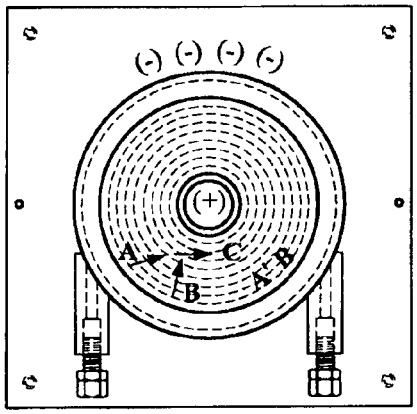

MOLECULAR MIMICRY

A ~ B → C
A' ~ B → NULL
A' IS ABERRANT TRASLATION
PRODUCT OF A

FIG. 6

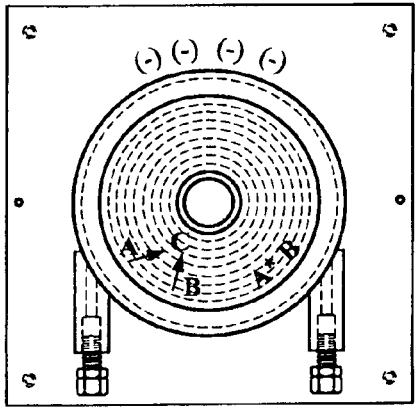

MOLECULAR CHIRALITY

A ~ B → C
A* ~ B → NULL
A* CHIRAL OPPOSITE OF A

FIG. 7

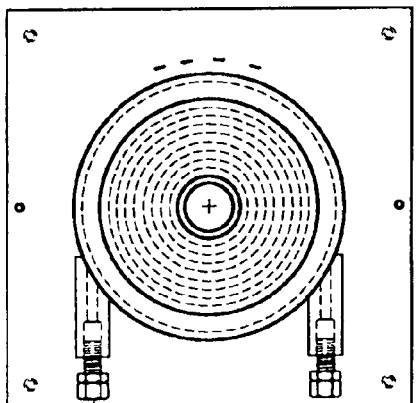

MOLECULAR EMULATION
OF WARM AND COLD BLOOD

↑ INPUT TEMPERATURE
REGULATED TO BE CONSTANT
VERSUS INPUT TEMPERATURE IS
COLD OR VARIABLE

FIG. 12

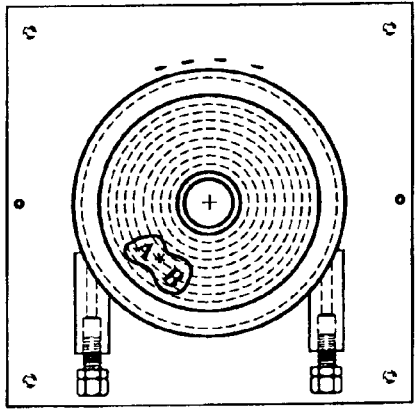

JUST NOTICEABLE
DIFFERENCE PHENOMENA

A ~ B ARE REAGENTS
WITHIN A "JUST NOTICEABLE"
DISTANCE - THE DEVICE AND
PROCESS CAPTURE INTERACTIONS
AS FUZZY AND ACCURATE PROCESSES

FIG. 13

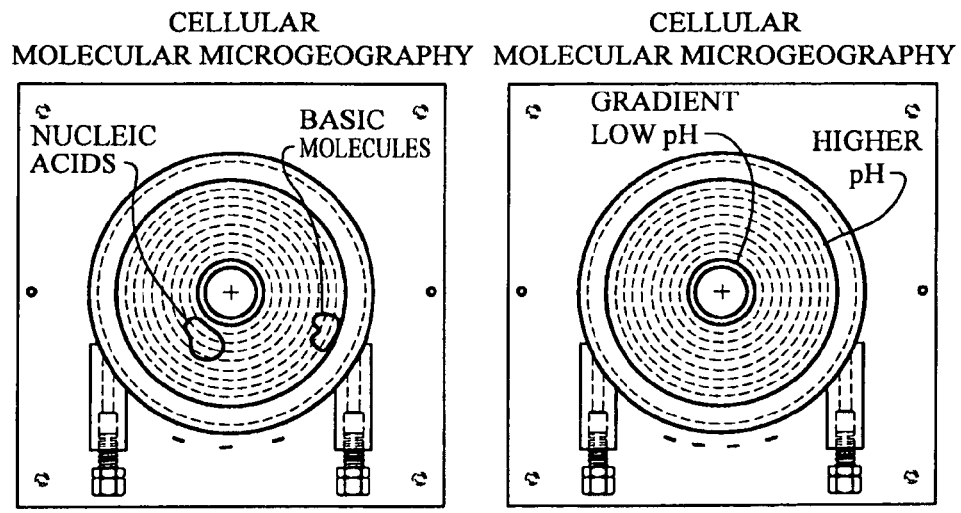
FIG. 8        FIG. 9
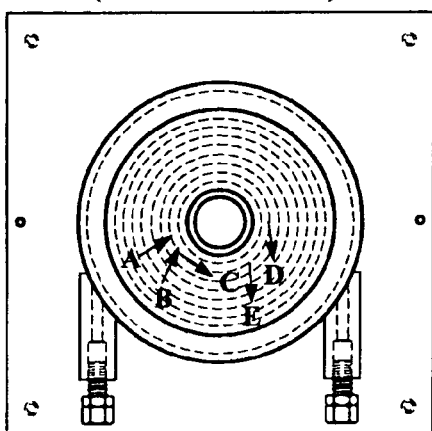
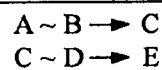
FIG. 10
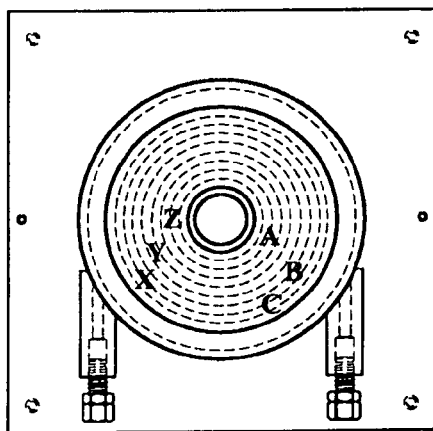
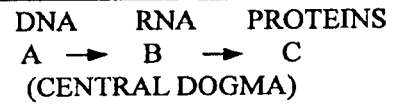
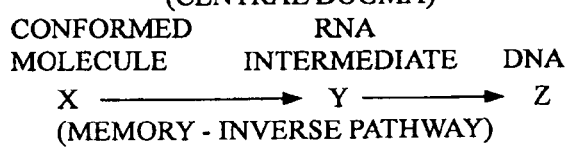
FIG. 11

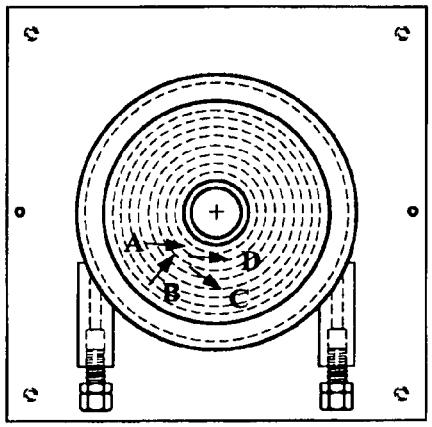

CONVERSION OF PROINSULIN TO INSULIN

A ~ B → C, D
A = PROINSULIN    C = INSULIN
B = TRYPSIN       D = C-REACTIVE PEPTIDE

FIG. 14

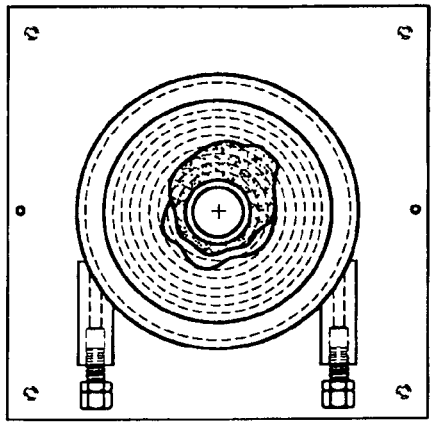

MICROGEOGRAPHY

D = DNA
SHADED AREA REPRESENTS NUCLEUS AND HIGHLY ACIDIC ENVIRONMENT

FIG. 15

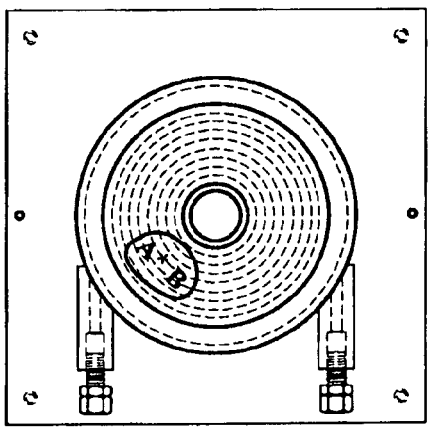

"JUST NOTICEABLE" CHEMISTRY

JUST NOTICEABLE DIFFERENCES BETWEEN MOLECULES PERMITS VISUALIZATION OF BIOCHEMICAL REACTION IN ENVIRONMENT ANALOGOUS TO IN VIVO ENVIRONMENT

FIG. 16

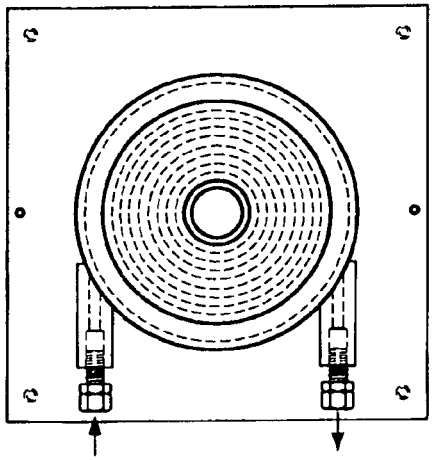

VARIABLE TEMPERATURE INPUT

OUTPUT
TO UNDERSTAND "COLD BLOODED" CHEMISTRY

FIG. 17

PRELIOPHIC MOLECULAR USING ELECTRIC FIELDS AND GRADIENTS FOR MANIPULATING MOLECULES

RELATED APPLICATIONS

This application is a divisional of U.S. application Ser. No. 10/879,627 of the same title, filed Jun. 29, 2004, now U.S. Pat. No. 7,826,974 B2, issued Oct. 2, 2014.

BACKGROUND OF THE INVENTION

This invention is termed a preliophic moleculator and process for moleculation as an abbreviated terminology for a protonic-electronic-ioni-c-photonic molecular computer. Preliophic is derived from the first two letters of words in the hyphenated description along with the last "ic", thereby creating the coined term. The preliophic molecular computer is a device used to manipulate the motion and interaction of selected molecules in a medium (e.g., polyacrylamide, agarose or starch gel) under the influence of an electric field, induced pH gradient, or by some other means. The device and process are invented to mimic features of inferred interactions of molecules in cellular structures. However, it is expected that the physical device has application beyond experimental studies in molecular and cell biology, and in producing molecular byproducts. It will comprise a useful tool in all fields of chemistry, including theoretical, conceptual, logical and mathematical studies involving molecular interactions in a controlled environment. Indeed, the conceptual embodiment of the physical device and process are central elements in several derivative novel, logical, albeit counterintuitive (i.e., non-obvious) claims. These include: vaccines for use in acquired immunodeficiency syndrome (AIDS) and other lentivirus-related infections involving single or multivalent killed vaccines against relatively uncommon pathogens, though not against the lentiviruses themselves; devices used in elucidating "autotoxicity," "autovirulence," and "context specificity"; conceptualizing a gedanken study designed to reveal both changes in DNA in brain and measure changing G*C::A*T ratios using single-nucleotide polymorphism (SNP) analyses involving DNA extracted from cells in a hair follicle and three sections in brain; and, non-invasive methods, approaches and technologies for measuring nurture quantitatively, in both living and artificial environments, by using G*C::A*T ratios. Each of these corollary inventions is claimed in this patent application.

Molecular interactions produced in preliophic moleculation processes and devices are a direct contrast to the lack of molecular interactions in electrophoresis and electrophoresis devices. That is, electrophoresis (in contrast to preliophic moleculation) facilitates parallel movements of molecules which, by definition of parallelism, cannot interact. Thus, the preliophic moleculator and its processes are useful in elucidating and disambiguating molecular function, whereas electrophoresis is useful in elucidating molecular structure.

Typically, the medium used with the preliophic moleculator device and process is a gel or substrate similar to types used in electrophoresis devices and processes, and especially medium used in isoelectric focusing (IEF). However, it is expected that other non-gel mediums also may prove useful (e.g., viscous fluids, polyacrylamides, or other compositions through which intact, non-denatured molecules are able to migrate under the influence of electric fields or gradients). In this description such substances are termed substrate mediums. (NB: Throughout this description, the term "mediums" deliberately is used as the plural of medium, to distinguish mediums from media.)

The impetus for this invention is a series of discoveries and inferences suggesting that parsimony exists among most, if not all, molecular mechanisms of long-term memories (LTM) in living systems accounting for evolution, speciation, development, differentiation, immunity, cognition and behavior, aging, and death. Central to that parsimony are changes in DNA, claims to the contrary notwithstanding. As examples, it generally is agreed that "selection" among random changes in DNA is a basis of Darwinian evolution. Barbara McClintock generally is credited with demonstrating that changes in DNA (dubbed transpositions or "transposons") account for the developmental process producing variegation in maize. Other changes in and to DNA (including methylation) are associated with development and differentiation from singular cell to multiple cell organisms. Susumu Tonegawa demonstrated that rearrangements in DNA are central to immune memory and recognition. Compelling evidence now suggests that LTM in brain must involve a priori changes in DNA, especially in non-proteomic regions of the genome, with subsequent a posteriori generation and development of axons and dendrites in the neural network.

Changes in DNA in brain differ fundamentally from changes in DNA described by McClintock and Tonegawa insofar as changes in DNA in brain are not accompanied by cell division. Evolutionarily, it is thought that the bony cranium served to constrain or ablate cell division, while retaining molecular mechanisms for changing DNA especially in brain. Equally important, cell division in brain would be counterproductive because of the information redundancy. In other words, redundancy derived from cell division and clonal expansion in the immune system is desirable, whereas the lack of cellular redundancy (albeit with increased neuronal axon and dendrite connectivity) in brain, serves to facilitate molecular information processing in neurons. In the end, those DNA changes in brain are not heritable and/or transmitted to germline cells (e.g., sperm and ova) thereby differing from both Darwinian and Lamarckian evolution. Indeed, a major reason for inventing the preliophic device and process is to provide a concrete embodiment of an inverse to Francis Crick's "central dogma." According to the "central dogma" molecular information generally flows from DNA to RNA (by a process called transcription), and from RNA to proteins (by a process called translation). Crick subsequently allowed for "reverse transcription" after the discovery of retroviruses, yet it is noteworthy that the "central dogma" was flawed at the outset. For this thesis and invention to be viable, there are no "dogma" regarding movements of molecules into, within and out of living cells beyond being directed and vectorial, and in a manner that permits interactions among other directed and vectorial molecules.

Four key, albeit unreported and non-obvious, observations provided an additional logical basis for this invention. First, although there is a well established chemio-osmotic hypothesis for energy production and electron transfer within mitochondria in cells, a purpose for hydrogen ion (i.e., proton) byproducts pumped from mitochondria was never fully elaborated. Second, microheterogeneous commercial amphoteric molecules (i.e., "ampholytes") used in IEF and other electrophoretic processes are remarkably analogous to and concordant with the microheterogeneity in natural intercellular microtubulin-associated proteins (also known as "microtubule associated proteins," [MAPs]), and phosphatidyl-proteins and other phosphatidyl-moieties associated with cell membranes (e.g., phosphatidylserine, phosphatidylinositol, phosphatidylinesitol, phosphatidylglycerol, phosphatidylethanolamine, phosphatidylethylamine). Third, the geometry of all electrophoretic devices, whether in one- or two-dimensional electrophoresis activities, is designed to examine and determine molecular structure based on parallel-movements of molecules in electric fields or proton gradients, with there being no potential for those devices to examine and determine molecular function. Structure is elucidated because molecular species move in parallel, with molecular weight and charge often serving to define structure. Fourth, cellular histology, a vast variety of reported and unreported clinical, pathological and experimental findings, and preliminary experimentation, all point to the logic of a "molecular computer" based on molecules moving toward their isoelectric points (pI), though interacting with other molecules moving toward their isoelectric points.

The invention reported here is initially comprised of a circular device supporting a type of IEF medium, typically a gel with one charged pole in the center and an oppositely charged pole, comprises the entire perimeter of the device. For example, with a positive pole at the center and the perimeter serving as the negative pole, electronegatively charged molecules will move toward the center and electropositively charged molecules will move towards the cell boundary (i.e., perimeter). This is precisely as it happens in cells wherein basic molecules generally move toward the perimeter of the cell where the pH is approximately 7.4, and acidic molecules generally move toward the center of the cell where the pH can be as low as 2 to 3. Even without its actual construction, this conceptual embodiment of a preliophic moleculator now provides a conceptual basis for cellular micro-geography thereby providing logical and theoretical reasons for the nucleus generally being situated in the center of cells where pH values are low, and other cellular structures being distributed more peripherally in cells, regardless of cell shapes. (NB: The term pH is a designation for the percentage of hydrogen ions. Also noteworthy is that shapes other than circular shapes work equally well in this invention, including triangles, pie-shapes, etc.).

A temperature regulated system is incorporated in the device both to accommodate the dissipation of heat and to regulate the rate molecules may move in their directed pathways. Not only does the temperature regulated system obviate denaturing molecules, it facilitates modeling cold-versus warm-blooded molecular information processing.

The terms, "moleculator" and "moleculation" are used, respectively, to define the device and process for inducing the controlled migration of molecules in a substrate medium under the influence of an electric field, pH-gradient or other means. Implied in the terminology is the study of the interaction of migrating molecules, or molecules that approach or have reached their isoelectric location. Also implied in the terminology is the study of arbitrarily close interacting molecules, whether these interactions take place at some pI or otherwise.

The design of the device is particularly adapted for the study of biological functions and processes, as the circular configuration emulates the generally spherical configuration of the biological cell. Avenues for studying the dynamics involved in the progression or expression of disease also are provided by use of the moleculator device. For example, although rarely discussed and despite its ubiquity, the Epstein-Barr virus (EBV) is associated with more than 92 different diseases and syndromes, some of which involve "hit-and-run" and/or "beneath-the-radar" pathology. Many of these 92 diseases and syndromes mimic or comprise psychosomatic illnesses that often are stress-induced. The intriguing question was why would a common and ubiquitous virus be associated with such a wide variety of diseases and syndromes, yet almost never do more than two of these 92+ diseases or syndromes occur in the same person? What possible molecular mechanisms could account for this counter-intuitive finding and seeming conundrum? What theories and technologies could answer these questions.

The terms "autotoxicity," "autovirulence" and "context-specificity" were coined in 1983 to explain these and other phenomena, including prion-related diseases. A prototype of autovirulence is specifically implicated in stress-induced EBV-associated consequences in HIV and AIDS (e.g., dose-dependent production of acid-labile alpha-interferon). There was other evidence of EBV-induced aberrant translation products associated with the EBER I and EBER II small nuclear ribonucleoproteins (snRNPS) [RNA plus protein particles]. Other viruses and their snRNPs also could contribute to the production of aberrant translation products (e.g., snRNPs comprising VA I and VA II associated with some adenoviruses), whereas lentiviruses (e.g., HIV) are more likely to be associated with aberrant transcription products. Finally, it was noted that extant theories of autoimmune diseases (e.g., that the immune system is abnormally reacting to "self") could give way to novel possibilities that "self" or "abnormal-self" are abnormally presented to a healthy immune system, possibly involving "molecular mimicry" of "self." What remained was to invent an appropriate and practical technology to explicate these theories, findings and other phenomena.

Evidence of EBV-associated aberrant translation products in a variety of EBV-associated diseases and syndromes was reported. Inferential evidence suggests EBER I and/or EBER II contribute to aberrant translation products and molecular mimicry. The preliophic molecular of this invention is designed to study molecular function and infer molecular mimicry experimentally, even in the absence of precise details of amino-acid sequences, conformational variations and/or molecular mechanisms. It is suggested that the etiology of EBV-associated diseases and syndromes ultimately can be unraveled with the aid of the preliophic molecular.

It is noteworthy that preliophic moleculation is unlike electrophoresis in at least one very significant regard. As noted, electrohoresis provides a simple, excellent and economical approach for purifying structure. By way of contrast, arbitrarily complex functional systems can be elucidated and explicated using preliophic moleculators. For example, the molecular biology, genetics and genomics of long-term memory (LTM) in living systems can be studied using the preliophic moleculator of this invention, and in some instance providing logical or mathematical proofs, against claims to the contrary notwithstanding.

A 1979 review by one of the inventors of six decades of research on molecular bases of LTM in living systems supports changes in DNA as a priori bases for LTM in bran, with axon-dendrite connectivity representing a posteriori bases for neural networks. Furthermore, no models of LTM are mathematically or logically complete without affirming or rejecting the claim that "the definitive evaluation of DNA as the ultimate repository of information" in brain (Smith 1979). The 1979 review then cited six novel lines of inquiry supporting the DNA change hypothesis. Two decades later, research involving five of six lines of inquiry now provides further evidence supporting DNA changes as a basis of LTM. Insofar as the device is designed to emulate molecular information flow at the cellular level, the preliophic moleculator now provides a means to examine a corollary to the remaining line of inquiry. In the end, preliophic moleculation enables one to model changing G*C::A*T ratios over time, both experimentally and concretely. At a practical level, this line of inquiry also implicates host mechanisms contributing to the microheterogeneity in lentiviruses, thereby contributing to the "proof" that neutralizing vaccines cannot be produced against HIV or other lentiviruses; that is, the intrinsic unreliability of reverse transcriptases and host factors contribute to entivirus microheterogeneity. Inferentially, the conceptual embodiment of the preliophic moleculator reveals possibilities for non-invasive imaging technologies to model changing G*C::A*T ratios over time in intact cells and organisms, and in advanced preliophic devices. Suc non-invasive imaging technologies most likely will focus on spin properties of phosphorus (in contrast to hydrogen) atoms in nuclear magnetic resonance studies.

If DNA in brain is subject to changes in association with LTM, it stands to reason that Francis Crick's "Central Dogma" of molecular biology is inadequate for explaining a necessary inverse flow of information possibly based on the input of conformational or other non-sequential representations of molecular information in contrast to sequential information embodied in the "central dogma." Interestingly, Crick may have anticipated this shortcoming given his little noted, albeit extraordinary, comment in a footnote: "There is, for example, the problem of the chemical nature of the agent of the disease scrapie." Nevertheless, we know enough to say that a non-trivial example showing that the classification was wrong could be an important discovery." This comment suggests a logical corollary about the flow of information in cells. Regardless, both pathways of information transfer [DNA to RNA to Proteins (connoted the "Central Dogma")] and an inverse pathway (conformational molecular information to endogenous- or exogenous-RNA-mediated reverse transcription (or other possible novel mechanisms) to changes in largely non-protein encoding regions of DNA) now can be studied in the invented preliophic moleculating device that emulates cellular molecular information processing (i.e., "moleculations"). Although there is not a Latinate term of art for this emulation process, preliophic molecular processes fall somewhere between being in vitro and in vivo. Indeed, preliophic moleculation, through its capture of functional molecular information processing, now makes it possible to educe mathematical and logical proofs that would not be possible in vivo and in vitro. The term "biological and chemical computability" is used to capture these logical and mathematical proofs, much akin and analogous to the notion of computability in computer sciences. The difference is that biological and chemical computability requires additional information about space, time, temperature and molecular vectorial positioning. As previously noted, this device and its moleculation processes also emulates artificial and cellular micro-geography positioned between in vivo and in vitro studies.

In the study of LTM and the evaluation of DNA as the ultimate repository of "information" (i.e., LTM) in the brain, the preliophic moleculator can aid in the empirical measurement and determination of DNA changes in the brain. The study of post-mortem brain tissue of exceptionally gifted individuals, descendants of such individuals at different ages, sets of identical twins raised together and apart, different sections of individual brains, and other such comparative studies, can be accomplished using the device of this invention. The potential for nuclear magnetic resonance studies already was cited. Use of fluorescent or other dyes also could find application, particularly in assessing changing G*C::A*T ratios.

Another complex conceptual embodiment of preliophic moleculation involves the study of causality in AIDS, and the formulation of vaccines for use in treating AIDS and other lentivirus infections. The former is mostly theoretical and inferential; the latter is largely empirical, though based on complex elements of the established cause. A brief sketch of the underlying reasoning follows.

Lentiviruses are one of three classes of retroviruses that produce changes in DNA when retrovirus RNA is "reverse transcribed" to form a DNA "provirus." A unique feature of lentiviruses—supported by a variety of clinical, experimental and epidemiological data—is that their proviruses generally occupy protected subclasses of cells in the immune system having LTM potential, which then are trans-activated by relatively uncommon nascent pathogens, though not relatively common pathogens. Other classes of retroviruses (i.e., oncoviruses and spumaviruses) generally lack trans-activation mechanisms, and generally do not occupy protected classes of immune system cells having LTM potential.

Although lentivirus trans-activation can be recursive in intact systems (i.e., lentiviruses can trans-activate themselves), lentivirus trans-activation most often is caused by relatively uncommon pathogens—so called opportunistic pathogens. Although distinctions between common and uncommon pathogens in AIDS have been known since the early 1980s, reasons for these distinctions remained elusive until the advent of conceptual preliophic moleculators.

Lentiviruses now provide a convenient means for highlighting several advanced preliophic moleculation applications possibly requiring multiple (and/or networked) preliophic devices. One application is to establish the cause of AIDS. To many scholars and investigators, HIV is the sine qua non for AIDS, whereas to others HIV may play no role in AIDS. Whether HIV is a necessary and sufficient element in AIDS, and the general matter of causality in AIDS has never been addressed; again, claims by O'Brien and Goedert (1996) to the contrary notwithstanding. Perhaps more broadly, are there necessary and sufficient rules or conditions required to establish causality in most infectious diseases? What roles can preliophic processes play in disambiguating these issues?

Among early attempts at defining conditions to establish causality are studies of anthrax by Robert Koch, based on work with his mentor, Jacob Henle. Koch formulated a set of postulates, often referred to as the Henle-Koch Postulates (HKP), which he sued in demonstrating that Bac illus anthracis is indeed the cause of anthrax. Four elements are central to Koch's "proof." First the pathogen must be isolated from the intact organism. Second, the isolated pathogen must be inoculated into a single cell-type, which, in turn, produces characteristic pathological changes. Third, the isolated pathogen must be transmitted to an animal model, causing like disease. Fourth, once isolated again from the animal model, the pathogen must be inoculated in species from which it was first inoculated, and then shown to cause the same underlying disease. A critical theme in these postulates is that a single cell-type links the pathogen to the disease. An underlying axiom from sentential logic captures the spirit of these HKP; to with, Modus Penendo Ponens (if "A implies B" is true; and, if "A" is true; then, "B" is true). That is, if Bacillus anthracis causes anthrax is true; and, if Bacillus anthracis is the true pathogen associated with anthrax; then, anthrax can be inferred (to be the true consequence of Bacillus anthracis).

If HIV and other lentivirus infections are to be shown to be causes of AIDS or other diseases using HKP, a single cell-type must be associated with disease. Not only is this not true based on clinical, laboratory, experimental and epidemiological evidence, preliophic moleculators bring this into sharper focus. Multiple cell-types are associated with diseases caused by relatively uncommon (nascent) "opportunistic" pathogens that trans-activate the HIV (or other lentivirus) provirus in a separate cell-type. Advanced preliophic moleculation processes will emulate networks of multiple preliophic moleculators—one set perhaps to emulate the consequences of trans-activation, and other sets perhaps to emulate associations between opportunistic pathogens and diseases.

Because HIV cannot be shown to be the sole or sufficient cause of AIDS using the HKP, what recourse is there? Proof lies in understanding distinctions between the effects of relatively common and uncommon pathogens in the HIV-infected individual (or in other lentivirus infections). There are compelling clinical, laboratory and epidemiological data that suggest that AIDS is not associated with relatively commonplace pathogens in HIV-infected persons. In short, a category of pathogens—so called relatively commonplace pathogens—do not play a role in trans-activating HIV. Indeed, considerable evidence suggests that the immune system remains intact for those pathogens. This finding can be emulated and modeled using preliophic moleculators, and give rise to applications of a second axiom from sentential logic; to with, Modus Tollendo Tollens (if "A implies B" is true; and, if "not B" is true; then, "not A" is true). Modus Tollendo Tollens sometimes is referred to as "the rule of denial." Application of this axiom, when B comprises the relatively commonplace pathogens in an environment, confirms clinical, epidemiologic and laboratory findings; to with, the cause of AIDS is HIV and selected relatively rare opportunistic pathogens. Although initially counterintuitive, an obvious corollary is that multivalent killed vaccines against relatively uncommon pathogens may circumvent trans-activation of HIV and other lentiviruses. This finding is affirmed in naturalistic studies involving Icelandic sheep between 1933 and 1954, simian AIDS-like diseases among primates in an animal colony at UC Davis during the late-1970s and mid-1980s, and in epidemiological data collected on human pathogens worldwide.

SUMMARY OF THE INVENTION

The preliophic moleculator or moleculation device and the moleculation process of this invention are devised to aid in the study of arbitrarily complex biological and chemical processes. They are particularly useful in studies of molecular genetics, proteomics and genomics. They also find applications in elucidating and explicating infectious diseases involving extant infectious microbes (e.g., viruses and prions), as well as other novel infectious subparticles implicated in autotoxicity, autovirulence and context specificity. A conceptual embodiment of multiple (and possibly networked) preliophic moleculators, when coupled with sentential logic, allows one to identify the cause of AIDS by emulating roles of both HIV and selected opportunistic pathogens, and to infer and invent multivalent killed vaccines against relatively uncommon pathogens as vaccines against AIDS. These multivalent killed vaccines are non-obvious and counterintuitive insofar as they are not directed against HIV, though they circumscribe and circumvent lentivirus trans-activation.

The moleculation device of this invention includes (but is not limited to) a circular apparatus with a structure supporting and containing an IEF medium, typically a kind of gel used in electrophoresis. The IEF medium or substrate medium has an annular configuration contained by a central hub and a perimeter. Included in the structure at the central hub and perimeter in contact with the substrate medium are electrode poles having opposite charges. This arrangement creates a concentric array that mimics a biological cell. Unlike rectilinear electophoretic analytic devices commonly utilized for molecular separations of compositions, the annular configuration divided into sectors provides opportunities for complex migrations with confluent mergers and collisional melding. By discrete placement of samples, osmotic diffusion as well as polar-directed migration is utilized in designing experimental processes.

The apparatus includes a cooling and temperature control system to both cool the substrate medium in a high voltage field and regulate the temperature of the substrate medium allowing experiments to be performed at different temperatures, for example, to simulate or emulate chemical processes in warm-blooded and cold-blooded animals. The cooling system includes a reservoir with a cooling coil having an external fluid input and output that is connectable to a fluid source such as a refrigerant or water supply.

With the exception of the poles and associated electronics, the apparatus is fabricated of a non-conductive material that does not chemically react with the reagents of the substrate medium or the substances being processed or analyzed. A clear plastic is preferred to allow observation of the substrate and cooling system to detect any reactions of visual interest or early manifestations of malfunction, particularly overheating. It is to be understood that the design of the apparatus described in this specification and shown in the drawings is a prototype for process experimentation, and, production units may differ in appearance, include minor changes or additions in function, and/or involve multiple networked units as in collections of cells comprising an organ or tissue.

The moleculation processes described in the specification are presented as examples of the process or method of moleculation using the unique type of apparatus described and are not intended to limit the scope or types of moleculation processes, both biological and chemical, intended to be covered by this specification. The process examples are conveniently described using a concentric array as a gradient overlay on a schematic representation of the apparatus and substrate. As noted, the concentric "bull's-eye" array may be divided into pie-shaped sectors for assisting in the setup and reporting of certain experiments. These and other features of the invention will become apparent from a consideration of the detailed description of the preferred embodiments.

BRIEF DESCRIPTION OF THE DRAWINGS

FIG. 6 is a diagrammatic schematic illustrating a process example of detection of molecular mimicry.

FIG. 7 is a diagrammatic schematic illustrating a process example of detection of molecular chirality.

FIG. 8 is a diagrammatic schematic illustrating a process example of producing a micro geography of separated substances.

FIG. 9 is a diagrammatic schematic illustrating a process example of producing a micro geography with molecular focusing.

FIG. 10 is a diagrammatic schematic illustrating a process example of convergent migration.

FIG. 11 is a diagrammatic schematic illustrating a process example of assisting in detecting molecular memory.

FIG. 12 is a diagrammatic schematic illustrating a process example of running at different temperatures.

FIG. 13 is a diagrammatic schematic illustrating a process example of detecting just noticeable difference phenomena.

FIG. 14 is a diagrammatic schematic illustrating a process example of observing staged biological processes.

FIG. 15 is a diagrammatic schematic illustrating a process example of mimicking a biological cell.

FIG. 16 is a diagrammatic schematic illustrating a process example of visualizing just noticeable chemistry.

FIG. 17 is a diagrammatic schematic illustrating a process example of understanding variable temperature by comparative analysis.

DETAILED DESCRIPTION OF THE PREFERRED EMBODIMENTS

Figure 1:
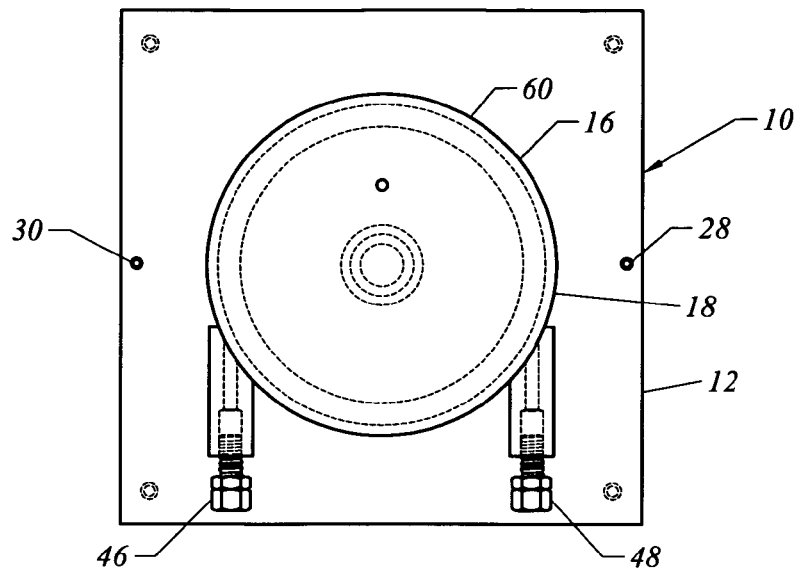
FIG. 1 is a top view of the preliophic moleculator of this invention.
Figure 2:
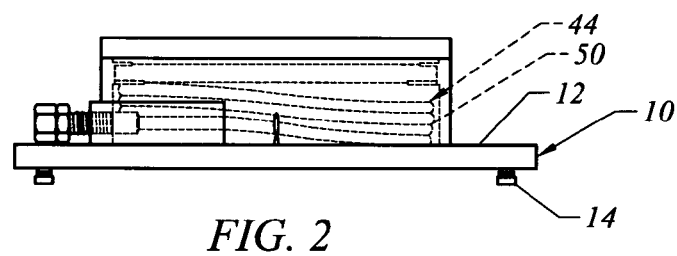
FIG. 2 is a side elevaional view of the moleculator of FIG. 1.
Figure 3:
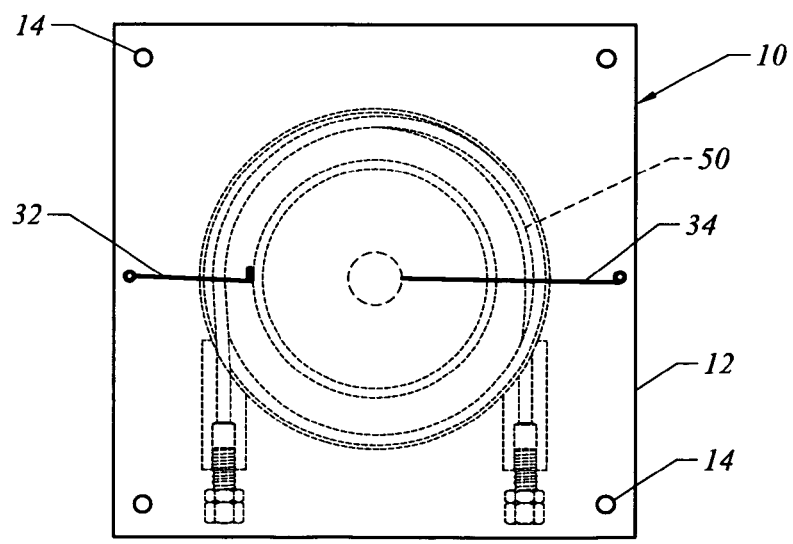
FIG. 3 is a bottom view of the moleculator of FIG. 1.
Figure 4:
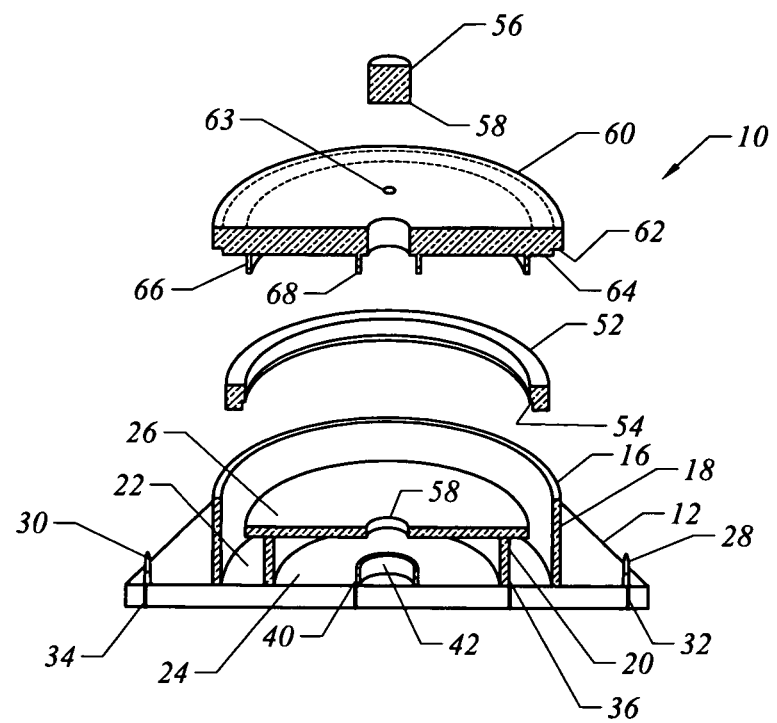
FIG. 4 is a cross-sectional exploded view of the moleculator of FIG. 1.
Figure 5:
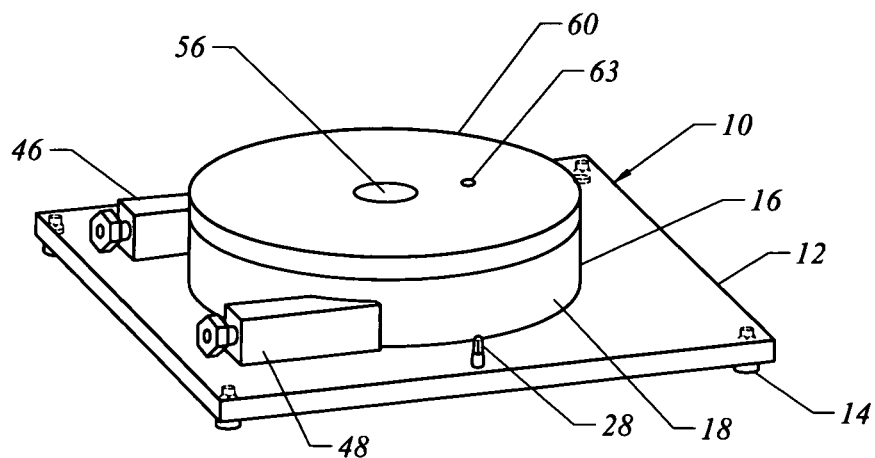
FIG. 5 is a perspective view of the moleculator of FIG. 1.

Referring to FIGS. 1-5, the preliophic moleculator of this invention is designated generally by the reference numeral 10 and comprises a moleculation apparatus for experimental testing of the movement and interation of molecules under the influence of an electrical field or induced gradient. The moleculation apparatus 10 includes a leveling base 12 with four corner leveling screws 14 that supports a circular containment structure 16. The containment structure 16 includes a circular perimeter wall 18 that forms a buffer dam to contain the buffer liquid that is typically salt water. A circular inner wall 20 concentric to the perimeter wall 18 separates an outer buffer chamber 22 from an inner buffer chamber 24. The inner wall 20 also supports a stage 26 for the substrate medium, typically a gel that is either precast or preferably cast in place using the auxilliary components of the moleculation apparatus 10.

Mounted on the leveling base 12 are two electrical terminals 28 and 30 which have separate conductors 32 and 34 running under the leveling base to wire electrodes 36 and 40 that respectively encircle the outside of the inner wall 20 and the outside of a concentric electrode mount 42. The electrical terminals 28 and 30 are connected to female jacks (not shown) of a direct current power source to provide the voltage required to create the electric field desired. Typically the voltage is in the hundreds of volts and is a function of the mobility of the particular molecules under study, the medium selected and the time allotted. As expected higher voltage will accelerate molecular migrations.

In order to prevent overheating and maintain a desired temperature allowing consistency in experiments, a cooling system 44 is included in the apparatus 10. The cooling system 44 includes an input connector 46 and an outflow connector 48 with a plastic cooling coil 50, shown in dotted line in FIGS. 2 and 3. The cooling coil 50 wraps around in the outer buffer chamber 24 and maintains the salt water buffer liquid at a desired temperature. It is to be understood that it is the substrate medium that is to be maintained at a desired temperature and that a system that maintained the substrate stage the desired temperature could be provided. In the system shown, by appropriately regulating the temperature of the cooling (or heating) water flowing through the coil 50, the temperature of the buffer fluid and hence the substrate medium is controlled.

Where the substrate medium is not pre-cast, the moleculation apparatus 10 includes a removable gel cast ring 52 having an undercut notch 54 allowing the gel cast ring 52 to seat on the substrate medium stage 26. Additionally, a center bung 56 with an undercut notch 58 is seated in a center hole 58 in the gel stage 26. The ring 52 and bung 56 provide a dam for the heated gel when poured onto the stage 26. Before the gel sets, a removable cover 60 having an undercut notch 62 and a vent hole 63 is seated on the perimeter wall 18. On the underside 64 of the cover 60 are a circular outer projecting rim 66 and a circular concentric inner projecting hub 68 which hang into the forming gel without touching the stage 26. When the gel sets, the cover 60, bung 56 and ring 52 are removed leaving a cast gel with an inner and outer impression which provides concentric reservoirs (not shown) for samples. Notably, the cover 60, which acts as a casting mold, can have a variety of different projecting elements configured for particular experiments. For example, the rim and hub can have a series of spaced notches which provide a series of spaced sample wells when the cover 60 is removed. After the samples are set according to the experiment contemplated, the substrate is filled before flooding. When operated, the buffer solution is raised over the substrate and the voltage is applied to the terminals. To protect a user from inadvertent electrical discharge and potentially hazardous shock, a plain cover without impression elements can be used during operation.

The moleculation apparatus 10 is fabricated from a clear plastic to permit observation of the migrations and reactions. Samples may be dyed to improve visualization. Electrodes are preferably platinum wire to resist corrosion but may be other corrosion resistant material and may be formed a ribbon.

Typically, the polarity of the electrodes is maintained with the outer electrode negative and the inner electrode positive. However, for a particular experiment it may be desirable to reverse the polarity with the outer electrode positive and the inner electrode negative. These and other modifications can be made to tailor the apparatus or alter the apparatus for a particular molecular manipulation.

FIGS. 6 through 17 provide exemplars of the variety of different moleculations that are possible when using the moleculation apparatus as a molecular computer.

In FIG. 6, detection of molecular mimicry may be accomplished by a convergent migration of molecule A and reactant molecule B on a path where a reaction product C is generated, but the convergent migration of an aberrant translation product of A, being A' when merged with B does not generate a reaction product C.

Similarly, in FIG. 7, when detecting molecular chirality, reacting molecule A with reactant molecule B generates a detectable molecule C, but A*, the chiral opposite of A generates null.

In FIG. 8, the moleculation apparatus is used to produce a micro geography of separated substances such as nucleic acids drawn to the positive electrode and basic molecules drawn to the negative electrode. Interaction could be determined by loading the substances at opposite poles with migration on a collision path for detection of reactivity before reaching their natural micro-geography.

In FIG. 9, micro-geography is similarly analyzed with molecular focusing depending on the pH of the substances in a substrate with and induced pH gradient, with molecules of low pH migrating toward the positive pole and molecules of high pH migrating toward the negative pole.

In FIG. 10, the moleculation apparatus is employed as a molecular computer for a complex reaction where A and B migrate on a convergent path producing C in a stable pH orbit. D migrates in an outward path reaches C to interact and produce the detected product E.

In FIG. 11, the moleculation apparatus is used to assist in detecting molecular memory vs. the central dogma and compares the conventional pathway of DNA (A) to RNA (B) to Proteins (C) with experimental pathways of Conformed molecule (X) to RNA intermediate (Y) to DNA (Z) that will confirm the inverse pathway hypothesis.

In FIG. 12, the moleculation apparatus is run at different or variable temperatures, for example to determine if a biological process varies in a warm blooded animal vs. a cold blooded animal.

In FIG. 13, the moleculation apparatus is used to detect the just noticeable difference phenomena. Reagents on a separate but merging path provide an opportunity to detect when their interaction is just noticeable, providing a means of capturing interactions as fuzzy and accurate processes.

In FIG. 14, the moleculation apparatus is used to observe staged biological processes, such as the conversion of proinsulin to insulin and biproducts, where Proinsulin (A) is on a convergent path with Trypsin (B) and reacts to produce Insulin (C) and (D) a C-reactive peptide.

In FIG. 15, the moleculation apparatus is used to mimic a biological cell with the micro-geography of the center being DNA representing the nucleus and a highly acidic environment.

In FIG. 16, the moleculation apparatus is used in just noticeable chemistry where A in the presence of B permits visualization of biochemical reaction in an environment analogous to in vivo environment.

In FIG. 17, the moleculation apparatus is used as a variable \ temperature device to understand "cold blooded" chemistry by comparative analysis with temperature as the variant.

It is to be understood that the foregoing exemplars are presented to demonstrate the different avenues that can be pursued when using the moleculation apparatus, and are not presented to limit the scope of this invention.

The invention claimed is:

1. A method of performing moleculation that stimulates the conditions of an eukaryotic cell for potential molecular interactions comprising the steps of:
   a. forming a stable, substrate medium adapted to accept a plurality of test samples having molecules with the characteristic of movement in the medium under the influence of an electric field, wherein the medium impedes movement of the molecules according to inherent characteristics of the molecules;
   b. establishing an electric field through the medium with an electropositive potential spatially displaced from an electronegative potential that is capable of inducing the vectorial molecular movement of the molecules in the test samples when placed in the medium between the electropositive potential and the electronegative potential, wherein the established electric field includes spaced, oppositely charged poles that are constructed to produce a non-orthogonal electro-potential field in the medium that induces non-parallel vectorial molecular movement of sample molecules in spatially separated test samples;
   c. placing two or more test samples in the medium at spatially separated locations, wherein the locations are selected relative to the established electric field between the electropositive potential and the electronegative potential such that the vectorial molecular movements of molecules in the respective spaced samples are such that the molecules migrate on paths in the medium under the influence of the electric field to move the separated molecules into closer proximity for potential molecular interactions.

2. The method of claim 1 wherein the established electric field is configured to induce vectorial molecular movement of the molecules in the spatially separated test samples in the medium on paths that tend to cause molecules in the spaced locations to collide.

3. The method of claim 1 wherein the established electric field is configured to induce vectorial molecular movement of the molecules in the spatially separated test samples in the medium on paths that tend to cause molecules in the spaced locations to converge.

4. The method of claim 1 wherein the oppositely charged poles are dissimilar in configuration.

5. The method of claim 1 wherein a first pole is circular and a second pole is displaced from the first pole and concentric to the first pole with the medium being located between the poles.

6. The method of claim 1 with the additional step before placing the samples in the medium of:
   controlling the temperature of the medium.

7. The method of claim 1 wherein the medium includes a buffering layer wherein electric current is passed through the buffering layer between the poles.

8. The method of claim 1 wherein the molecules of the samples are induced to move to the molecules' isoelectric point.

9. The method of claim 1 including the step of adding an imaging substance to enable image capture of molecular migrations in the medium.

10. A method of moleculation that induces the directional migration of molecules in any non-denaturing electrophoretic substrate medium for investigating the potential interactions of molecules in test samples comprising the steps of:
    a. forming an electrophoretic substrate medium adapted to accept a plurality of test samples having molecules with the characteristic of movement in the medium under the influence of an electric field;
    b. establishing an electric field through the medium with an electropositive potential spatially displaced from an electronegative potential that is capable of inducing the vectorial molecular movement of the molecules in the test samples when placed in the medium wherein the established electric field includes spaced, oppositely charged poles that are arranged with respect to the medium to generate an electromotive force that induces non-parallel vectorial molecular movement of the molecules in the spatially separated test sample, wherein the poles are oppositely charged and constructed to produce a non-orthogonal electro-potential field in the medium;
    c. placing two or more test samples in the medium at spatially separated locations, wherein the locations are selected relative to the established electric field such that the vectorial molecular movements of molecules in the respective spaced samples are such that the molecules migrate on paths in the medium under the influence of the electric field to move the separated molecules into closer proximity for potential interaction.

11. The method of claim 10 wherein the established electric field is configured to induce vectorial molecular movement of the molecules in the spatially separated test samples in the medium on paths that tend to cause molecules in the spaced locations to collide.

12. The method of claim 11 wherein the established electric field is configured to induce vectorial molecular movement of the molecules in the spatially separated test samples in the medium on paths that tend to cause molecules in the spaced locations to converge.

13. The method of claim 10 with the additional step before placing the samples in the medium of:
    controlling the temperature of the medium.

14. The method of claim 10 wherein the medium includes a buffering layer wherein electric current is passed through the buffering layer between the poles.

15. The method of claim 10 wherein the molecules of the samples differ and are induced to move to the molecules' isoelectric point.

16. The method of claim 10 including the step of adding an imaging substance to enable image capture of molecular migrations in the medium.

* * * * *